(12) United States Patent
Bral (10) Patent No.: US 8,881,920 B1
(45) Date of Patent: Nov. 11, 2014

(54) AUTOMATICALLY RINSING BABY BOTTLE

(71) Applicant: Hooshang Bral, Beverly Hills, CA (US)

(72) Inventor: Hooshang Bral, Beverly Hills, CA (US)

( * ) Notice: Subject to any disclaimer, the term of this patent is extended or adjusted under 35 U.S.C. 154(b) by 0 days.

(21) Appl. No.: 14/094,502

(22) Filed: Dec. 2, 2013

(51) Int. Cl.
*A61J 9/00* (2006.01)

(52) U.S. Cl.
CPC ............... *A61J 9/008* (2013.01); *Y10S 215/08* (2013.01)
USPC ............ 215/6; 215/11.1; 215/11.2; 215/11.4; 215/11.6; 215/DIG. 8; 222/142.5; 222/563

(58) Field of Classification Search
USPC ................ 215/6, 11.1, 11.2, 11.4, 11.5, 11.6, 215/DIG. 8; 222/142.5, 464, 563
See application file for complete search history.

(56) References Cited

U.S. PATENT DOCUMENTS

| | | | |
|---|---|---|---|
| 2,655,279 A | 10/1953 | Wolf | |
| 2,680,441 A | 6/1954 | Krammer | |
| 2,786,769 A | 3/1957 | Greenspan | |
| 2,984,377 A * | 5/1961 | Biondi | 215/11.1 |
| 3,741,383 A | 6/1973 | Wittwer | |
| 4,410,085 A | 10/1983 | Beneziat et al. | |
| 4,548,339 A | 10/1985 | Gorman | |
| 4,821,895 A | 4/1989 | Roskilly | |
| 4,856,995 A | 8/1989 | Wagner | |
| 4,940,152 A | 7/1990 | Lin | |
| 5,029,701 A | 7/1991 | Roth et al. | |
| 5,244,122 A | 9/1993 | Botts | |
| 5,437,381 A | 8/1995 | Herrmann | |
| 5,617,966 A | 4/1997 | Bral | |
| 5,897,007 A * | 4/1999 | Schein et al. | 215/11.1 |
| 5,960,971 A * | 10/1999 | Bral | 215/11.4 |

FOREIGN PATENT DOCUMENTS

| | | |
|---|---|---|
| FR | 1288859 | 3/1962 |
| GB | 2285790 | 7/1995 |
| WO | WO9524177 | 9/1995 |

* cited by examiner

*Primary Examiner* — Elizabeth Volz
(74) *Attorney, Agent, or Firm* — Cislo & Thomas, LLP (57) ABSTRACT

A nursing bottle for automatically rinsing a baby's teeth by independently dispensing first and second liquids, includes a nursing bottle having a nipple, a rinsing device having a dispensing end and a plurality of dispensing holes adjacent to the dispensing end for retaining the second liquid within the rinsing device while the nursing bottle receives the first liquid, and dispensing the second liquid automatically when the first liquid has been substantially depleted. The second liquid remains retained within the rinsing device when the bottle is at least substantially inverted due to the pressure of the first liquid at the dispensing holes and the vacuum created inside the rinsing device. When the first liquid is depleted sufficiently to expose at least one dispensing hole, the pressure is released, air is introduced into the rinsing device and the second liquid is dispensed through the other dispensing hole. As a result, the second liquid is automatically released from the rinsing device and into the nipple to rinse the baby's teeth at the proper time.

15 Claims, 10 Drawing Sheets

AUTOMATICALLY RINSING BABY BOTTLE

TECHNICAL FIELD

This invention relates generally to a nursing bottle, and more particularly to a nursing bottle for babies, which automatically rinses the babies' teeth after the contents of the nursing bottle have been emptied by dispensing a first liquid and subsequently dispensing a second liquid after the first liquid, thus preventing decay of the babies' teeth.

BACKGROUND

Typically, a baby goes to sleep after drinking a bottle of milk or formula from a nursing bottle. Likewise, a baby will fall completely asleep with a nursing bottle in its mouth while still drinking from the bottle. This results in the milk or other contents from the nursing bottle maintaining contact with the baby's teeth for extended periods of time which results in tooth decay of the baby's teeth.

A number of improvements have been made to the conventional nursing bottle for administering a second liquid which is distinct from the contents of the nursing bottle. However, these improvements have typically been in the area of medicine dispensing in connection with a nursing bottle. In these systems, a conventional baby bottle has a tube or syringe either within the bottle or on the exterior of the bottle. A first solution such as baby formula is placed within the bottle while medicine is placed within the tube. The two solutions are either mixed prior to administering both solutions to the baby or the second solution is manually released into the baby's bottle while the baby is ingesting the first solution. In both systems, the second solution is released manually and prior to the first solution being substantially emptied from the bottle.

For example, U.S. Pat. No. 2,680,441 to Krammer, issued Jun. 8, 1954, discloses a nursing bottle having a separate syringe attached to the nipple of the nursing bottle. The syringe contains a rubber bulb adjacent to the closed end of the bottle which must be manually depressed to empty the contents of the syringe.

U.S. Pat. No. 4,821,895 to Roskilly, issued Apr. 18, 1989, discloses a nursing bottle having a separate syringe attached to the nipple in a similar manner as the Krammer reference. The plunger of the syringe must be manually depressed to administer the contents of the syringe into the nipple of the nursing bottle.

Likewise, U.S. Pat. No. 5,244,122 to Botts, issued Sep. 14, 1993, also discloses a nursing bottle having a manually operated syringe disposed within the nursing bottle. However, as with the prior art, the plunger of the syringe must be manually operated, which is inconvenient.

A related type of nursing bottle comprises two separate compartments within the nursing bottle, wherein one compartment is punctured to release the contents into the second compartment. For example, U.S. Pat. No. 2,786,769 to Greenspan, issued Mar. 26, 1957, discloses a nursing bottle having an inner compartment which is punctured using a threaded shank or screw, which must be manually operated from the exterior of the nursing bottle. The Greenspan reference, however, does not rinse the baby's teeth as it is incapable of delivering a first liquid of the nursing bottle and subsequently delivering a second liquid to the baby. Instead, Greenspan discloses the manual mixing of both liquids prior to delivery of the solution to the baby.

Similarly, U.S. Pat. No. 3,741,383 to Wittwer, issued Jun. 26, 1973, discloses a nursing bottle having an inner compartment which is punctured with a sharp object such as a needle prior to administering the contents of the nursing bottle to the baby.

Another nursing bottle design is disclosed in U.S. Pat. No. 2,655,279 to Wolf, issued Oct. 13, 1953, wherein a flexible tube having a weighted end is placed within the nursing bottle. The tube has a hollow bore running throughout which allows passage of the contents of the nursing bottle to the nipple. The first end of the tube is attached to the nipple while the second end of the tube is placed near the bottom surface of the nursing bottle. The weighted member enables the tube to bend when the nursing bottle is moved from a vertical to a horizontal orientation. As a result, the second end of the tube remains submerged in the contents of the nursing bottle regardless of the orientation of the bottle thereby eliminating the excessive intake of air. However, this nursing bottle does not provide two separate compartments for independently delivering two separate liquids but instead provides a tube for delivering only one liquid.

Medicine dispensing nursing bottles are known and disclosed in, for example, U.S. Pat. No. 5,029,701 to Roth at al., issued Jul. 9, 1991, which has a medication vile disposed within the bottle. However, this nursing bottle does not allow any liquid to be dispensed from within the bottle itself but only from the medication vile which is completely sealed in relation to the nipple. Therefore, the bottle only houses the vile and is not in open communication with it.

In another design, a rinsing device is used, but a valve is required to open and close dispensing holes at the appropriate time. Moving parts, however, make the device more difficult to clean and more costly to manufacture. In addition, the moving valve can stick. Also, due to the moving valve and the positioning of the dispensing holes, the second liquid may be discharged prematurely, thereby preventing the first liquid from clearing out substantially from the nipple before the second liquid is dispensed. This causes a substantial amount of the first liquid to mix with the second liquid, thereby diminishing the rinsing effect of the second liquid. Furthermore, the valve embodiment is limited by the angled positioning of the rinsing device. For example, if the rinsing device is horizontal or near horizontal, the valve will not slide to expose the dispensing holes due to the lack of gravitational pull in the proper direction. If the rinsing device is completely vertical, air cannot enter through the dispensing holes.

Accordingly, it would be desirable to provide a nursing bottle capable of delivering a first liquid to a baby, such as baby formula, and then rinsing the first liquid from the baby's mouth by subsequently delivering a second liquid, such as fluoride water, wherein the second liquid is delivered automatically upon the first liquid being substantially dispensed from the bottle without the need for moving parts. In addition, there is a need for an automatically rinsing baby bottle that can automatically dispense a second liquid while a baby is drinking from the baby bottle regardless of the angle or orientation of the bottle.

SUMMARY

Accordingly, it is an object of the present invention to provide an improved nursing bottle for rinsing a baby's teeth after drinking formula from the nursing bottle.

It is a further object of the present invention to provide a nursing bottle for rinsing as baby's teeth by automatically dispensing a second liquid subsequent to a first liquid, when the first liquid is substantially depleted.

It is a further object of the present invention to provide a nursing bottle that can dispense a second liquid regardless of the relative position of the baby bottle to the baby's mouth so long as the bottle is positioned to allow the baby to drink from the bottle.

In carrying out the above and other objects of the invention in one form, there is provided as nursing bottle, comprising a bottle, rinsing device having a plurality of openings and/or tubes, and a nipple. The bottle has an open end for receiving the first liquid and a second closed end for retaining the first liquid. The rinsing device, configured to be housed in the bottle and store a second liquid, has a dispensing end adjacent the open end of the bottle for dispensing the second liquid within the bottle. The nipple is mounted on the open end of the bottle for dispensing the first and second liquids to the baby through the discharge hole of the nipple. The openings or tubes are positioned adjacent the dispensing end of the rinsing device for retaining the second liquid within the rinsing device when the bottle is at least substantially inverted until the first liquid drops below at least one hole or tube. As a result, the rinsing device automatically releases the second liquid into the nipple to rinse the baby's teeth.

DETAILED DESCRIPTION OF THE INVENTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

Referring to the figures, a nursing bottle 1 for babies includes a conventional bottle 2 having a screw-threaded neck 3 defining an opening 14, an end wall 9 opposite the opening 14, an annular screw-threaded bottle top 4, and a rubber teat or nipple 5 defining a discharge hole 15, as is well known in the art.

A rinsing device 50 is configured to be housed inside the nursing bottle 1. Preferably, the rinsing device 50 is in the form of a hollow tube 6, positioned along a vertical axis 16 of the bottle 2. The tube 6 has first and second ends 7 and 8, respectively, wherein the first end 7 or dispensing end may have an opening 13 which is positioned in proximity to the nipple 5 while the second end 8 is positioned in proximity to the end wall 9 of the bottle 2. The second end 8 may be attached, either permanently or releasably, to the end wall 9, but is preferably unattached. Therefore, when the rinsing device 50 is properly positioned inside the bottle 2, as shown in FIG. 1, 4, 6 or 8 two separate cavities are defined. The first cavity 52 is defined by the inner side wall 18 of the bottle 2. The second cavity 54 is defined by the inner side wall 64 of the rinsing device 50. The first cavity 52 receives a first liquid 70, such as milk, baby formula, or some other nutritional liquid, while the second cavity 54 receives a second liquid 72, such as water, a fluoride solution, or some other rinsing liquid.

The rinsing device 50 is configured to be placed inside the bottle 2. The rinsing device 50 comprises at least one side wall 64 for storing the second liquid 72. In the preferred embodiment, the rinsing device 50 is cylindrical in shape having a dispensing end 7, and a closed end 8 opposite the dispensing end 7. The rinsing device 50 can have any other cross-sectional shape, such as oval, triangular, square, rectangular, pentagonal, hexagonal, etc., thereby having multiple side walls.

When the rinsing device 50 is properly placed inside the bottle 2, the dispensing end 7 of the rinsing device 50 is adjacent to the open end 14 of the bottle 2. The closed end 8 of the rinsing device 50 may be situated at the closed end 9 of the bottle 2. In some embodiments, to increase the volume capacity of the first liquid 70 in the bottle 2, the rinsing device 50 may be shortened and seated on radially inward protrusions from the inner wall 18 of the bottle 2. The positioning of the protrusions should be in a manner such that when the rinsing device 50 is seated on the protrusions, the dispensing end 7 of the rinsing device 50 is adjacent to the open end 14 of the bottle 2.

Figure 1:
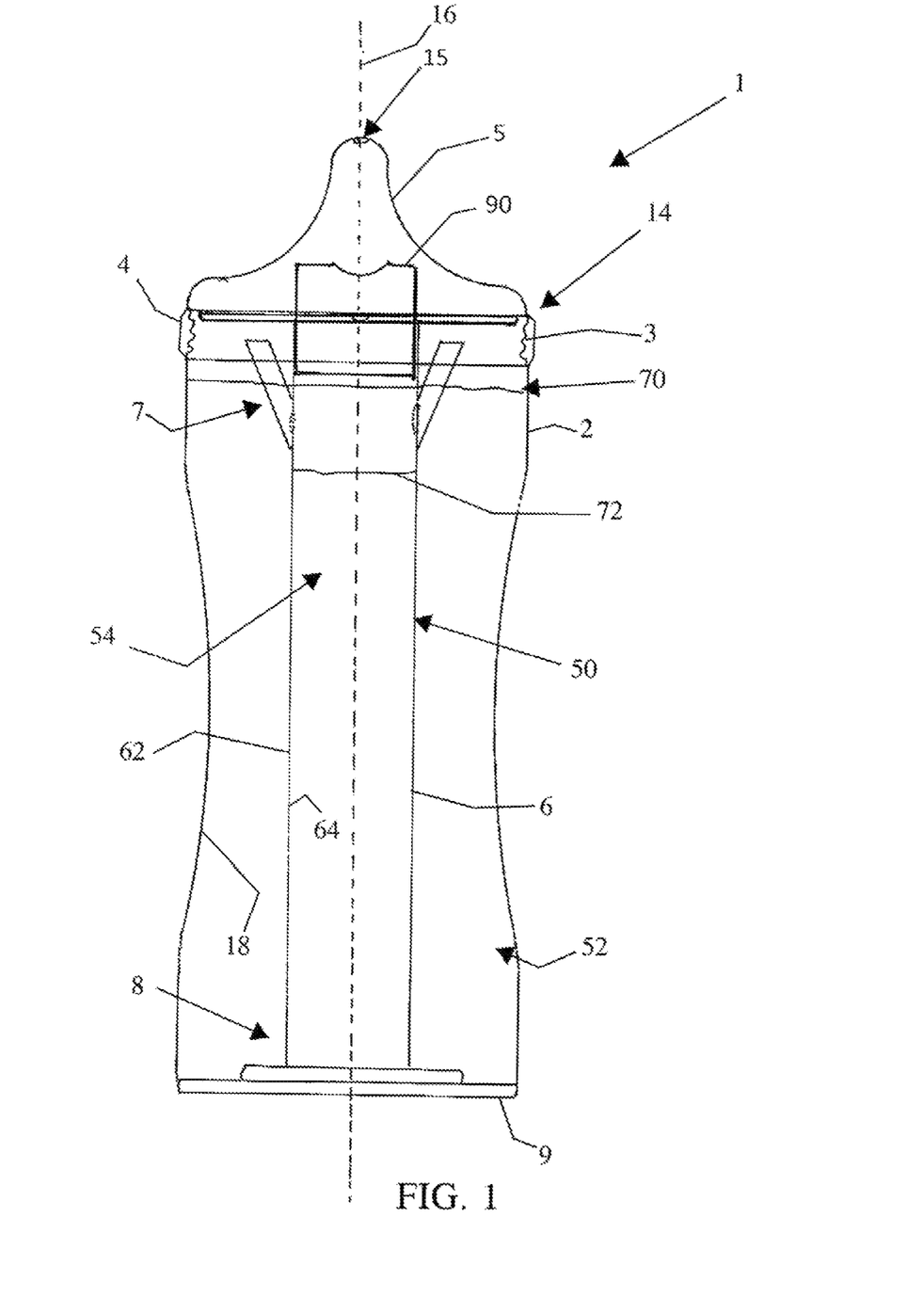
FIG. 1 is an elevation view of an embodiment of a nursing bottle of the present invention.
Figure 2:
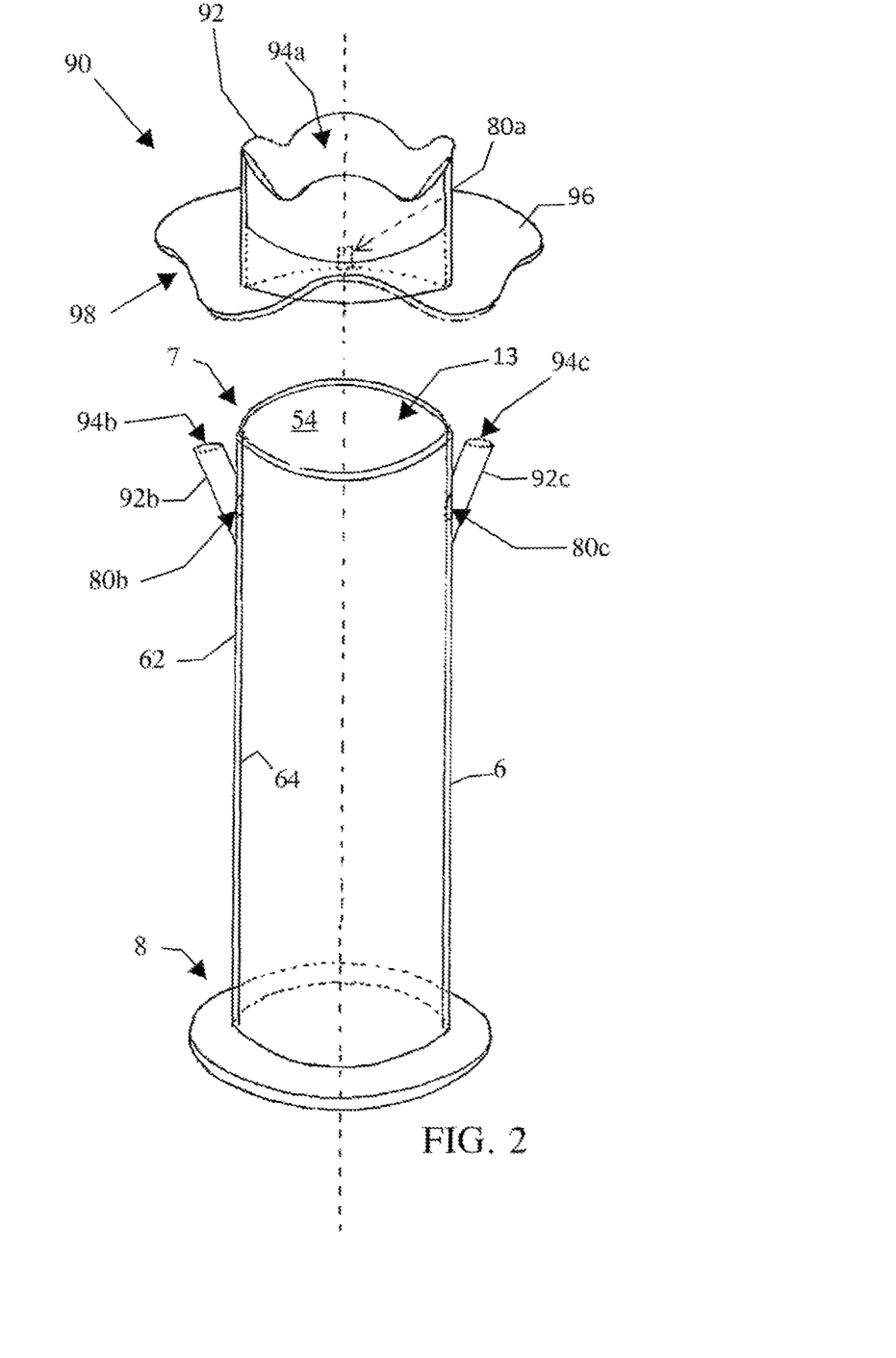
FIG. 2 is an exploded view of an embodiment of a rinsing device of the present invention.
Figure 3A:
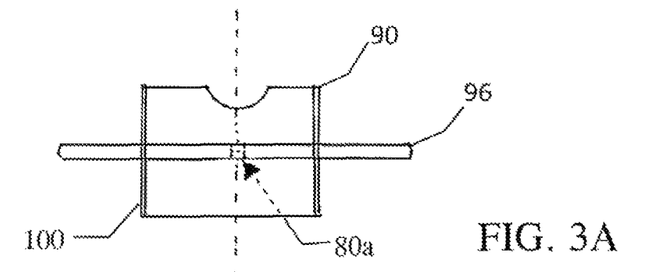
FIG. 3A is a side view of an embodiment of a removable cover.
Figure 3B:
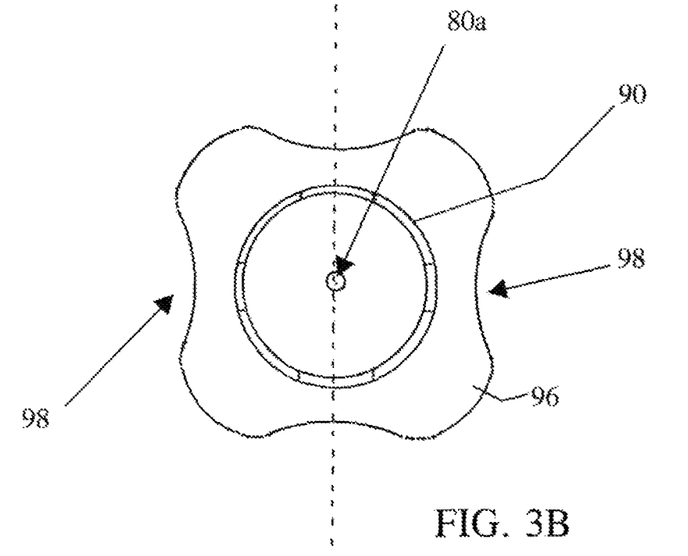
FIG. 3B is a top view of the removable cover shown in FIG. 3A.
Figure 4:
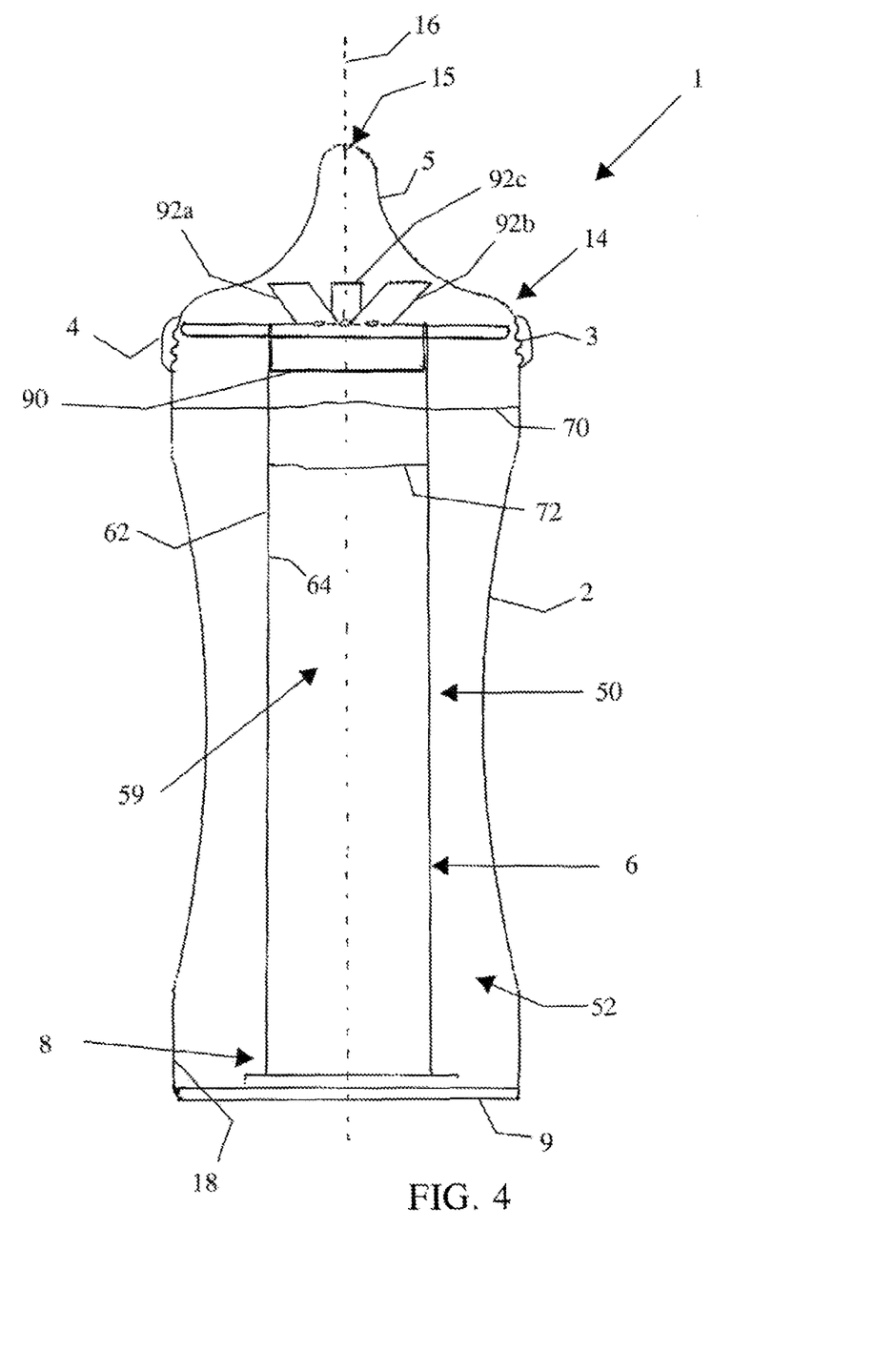
FIG. 4 is an elevation view of an embodiment of the present invention.

The rinsing device 50 defines at least one dispensing holes 80*a-c* adjacent or near the dispensing end 7. In some embodiments, the dispensing holes 80*a-c* are on the side wall 64 of the rinsing device 50 as shown in FIGS. 1 and 2. In some embodiments, the dispensing holes 80*a-c* may be on a top wall or a cover 90 as shown in FIGS. 1-10B. The dispensing holes 80*a-c* allow the second fluid 72 to be dispensed from the rinsing device 50 by allowing air to enter through at least one of the dispensing holes while the second liquid 72 is released from another dispensing hole. The dispensing holes 80*a-c* can release the second liquid 72 directly into the bottle 2, or through an opening 94*a-d* of a tube 92*a-c* connected to the rinsing device 50 at a dispensing hole 80*a-c*. In the preferred embodiment, the dispensing holes 80*a-c* should be small enough such that when the rinsing device 50 is inverted, and air is unable to enter through any of the dispensing holes 80*a-c*, the second liquid 72 cannot escape through the dispensing holes 80*a-c*. In the preferred embodiment, the dispensing holes 80*a-c* are 1 mm to 5 mm in diameter. Preferably, the dispensing holes are 1 mm to 3 mm in diameter.

The cover 90 may be a removable cover so as to expose the main opening 13 of the dispensing device 50 to fill the dispensing device 50 with the second liquid 72. The cover 90 may be defined by a side wall 100 dimensioned substantially similar to the side wall 64 of the rinsing device 50 so as to create a resistance fit. In some embodiments, the cover 90 or side wall 62 may have tubes 92*a-c* with openings 94*a-d* in fluid communication with the dispensing holes 80*a-c*. In the preferred embodiment, the openings 94*a-d* of the tubes 92*a-c* are uncovered or unobstructed, meaning there are no fixed or moveable physical obstructions are barriers created by any portion of the nursing bottle 1 or rinsing device 50 that would prevent, hinder, or obstruct the flow of the second liquid 72 through the openings 94*a-d*.

In use, when the rinsing device 50 and the bottle 2 are inverted, the openings 94*a-d* remain submerged in the first liquid 70 when a substantial amount of the first liquid 70 remains in the bottle 2. The first liquid 70 creates pressure against the openings 94*a-d* and/or the dispensing holes 80*a-c*, and prevents any air from entering into the rinsing device 50. This causes the second liquid 72 to remain in the rinsing device 50. When the first liquid 70 is sufficiently depleted so as to expose one of the openings 94*a-d*, air is allowed in through one of the openings (e.g. 94*c*) and into its respective dispensing holes (e.g. 80*c*), which causes the second liquid 72 to be released through another dispensing hole (e.g. 80*a*) and its respective opening (e.g. 94*a*).

Figure 5A:
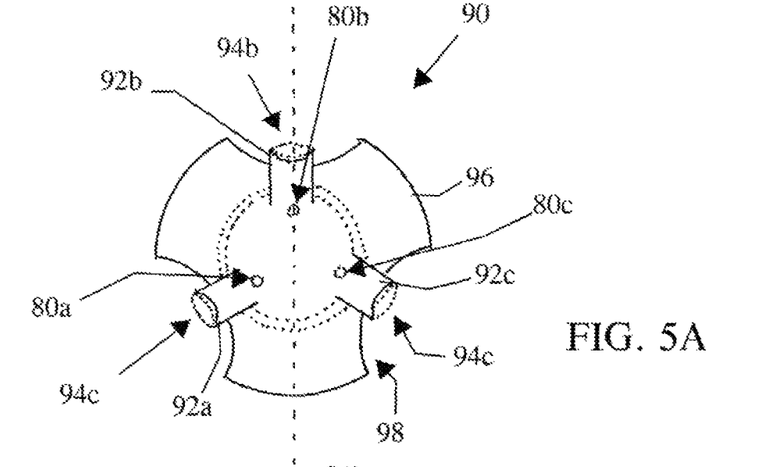
FIG. 5A is a top view of the removable cover shown in FIG. 4.

In some embodiments, the rinsing device 50 comprises one or more tubes 92*a-c* attached to or integrally formed with the outer side wall 62 or cover 90 at least one of the dispensing holes 80*a-c*. The tubes 92*a-c* are hollow having the openings 94*a-d* on the free ends, which are in fluid communication with their respective dispensing hole 80*a-c*, through which the second fluid 72 can be dispensed or air introduced. Each tube 92*a-c* may have one or more openings 94*a-d*. The openings 94*a-d* may be on the tops of the tubes 92*a-c* or on the sides of the tubes 92*a-c*. Preferably, the rinsing device 50 comprises a plurality of tubes 92*a-c*, one for each of the dispensing holes 80*a-c*. In the preferred embodiment, at least some of the plurality of dispensing holes 80*a-c* and their respective tubes 92*a-c* are evenly and angularly spaced apart about the side wall 62 or cover 90 as shown in FIGS. 2, 5A, 7A-7C, 9A-9B, and 10A-10B. For example, if two dispensing holes 80*b*, 80*c* are on the side wall 62 or cover 90, then the two dispensing holes 80*b*, 80*c*, may be angularly spaced apart by about 180 degrees as shown in FIG. 2. If there are three dispensing holes 80*a-c*, all on the side wall 62 or cover 90, then the three holes may be angularly spaced apart by about 120 degrees as shown in FIG. 5A, and so on. Having multiple dispensing holes 80*a-c* evenly and angularly spaced apart about the side wall 62 or cover 90 allows the nursing bottle 1 to be used as intended regardless of the orientation of the bottle 1 held by the baby. Therefore, while the baby is drinking from the nursing bottle 1, as the first liquid 70 exposes one of the openings (e.g. opening 94*c*), the respective dispensing hole 80*c* becomes an aerating hole to allow air into the rinsing device 50. This causes the second liquid 72 to dispense from the other dispensing hole (e.g. dispensing hole 80*b*) and opening (e.g. opening 94*b*).

The removable cover 90 was have an extension 96 extending radially outwardly towards the side wall 18 of the bottle 2 to minimize lateral movement of the rinsing device 50 while inside the bottle 2. An opening is required to allow the first liquid to pass through the extension 96. Therefore, in some embodiments, the extension 96 may define a gap 98 between the removable cover 90 and the side wall 18 of the bottle 2. The gap 98 may be created by holes, cutouts, undulations, and the like, within the extension 96.

In some embodiments, as shown in FIGS. 4-10B, all of the dispensing holes 80*a-c* may be on the removable cap 90. The remaining essential features are the same or similar to that of the embodiment shown in FIGS. 1-3B except as indicated otherwise. The dispensing holes 80*a-c* may have associated with it tubes 92*a-c*, one tube attached to or integrally formed with the cover 90 at one dispensing hole 80*a-c*. Each tube 92*a-c* may be hollow and have an opening 94*a-d* at its free end having fluid communications with its respective dispensing hole 80*a-c*. The openings 94*a-d* at the free end may be at the top of the tubes 92*a-c* as shown in FIGS. 5A, 5B. In some embodiments, the openings 94*a-d* at the free end may be on the side wall defining the tubes 92*a-c*, as shown in FIGS. 8-10B.

When tubes 92*a-c* are used, the openings may range from approximately 1 mm to approximately 12 mm in diameter. However, when the openings 92*a-c* have a large diameter (e.g. greater than approximately 3 mm) then the diameter of the dispensing hole 80*a-c* should be small (e.g. approximately 3 mm or less). In embodiments in which tubes 92*a-c* are used, if the opening 94*a-d* in the tubes are small (e.g. approximately 3 mm or less), then the diameter of the dispensing holes 80*a-c* can be large (e.g. greater than approximately 3 mm).

Preferably, when the openings 94*a-d* are on the sides of the tubes 92*a-c* the openings 94*a-d* may be approximately 1 mm to approximately 3 mm. When the openings 94*a-d* are on the tops of the tubes 92*a-c*, the openings 94*a-d* may be approximately 3 mm to 12 mm in diameter.

Preferably, the plurality of dispensing holes 80*a-c* and their respective tubes 92*a-c* are evenly and angularly spaced apart about the removable cover 90.

Figure 5B:
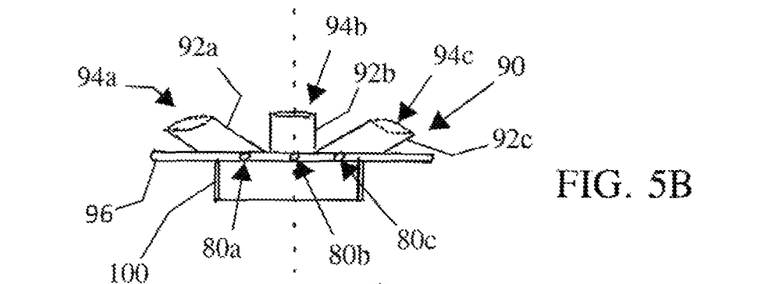
FIG. 5B is a side view of the removable cover shown in FIG. 5A.
Figure 5C:
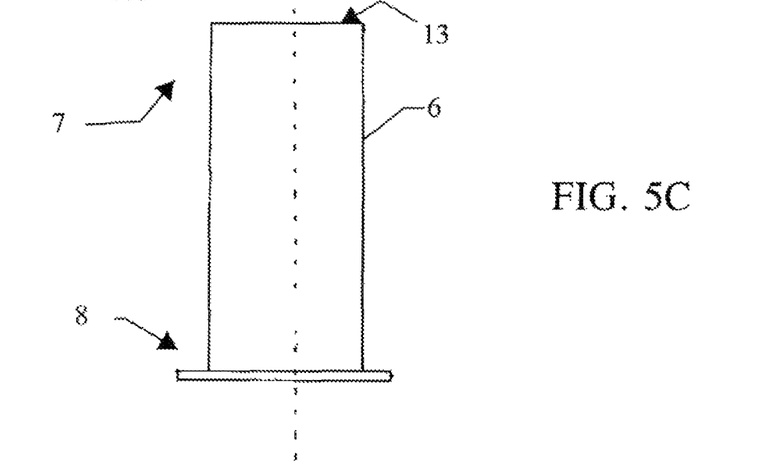
FIG. 5C is an elevation view of the rinsing device shown in FIG. 4 with the removable cover removed.
Figure 8:
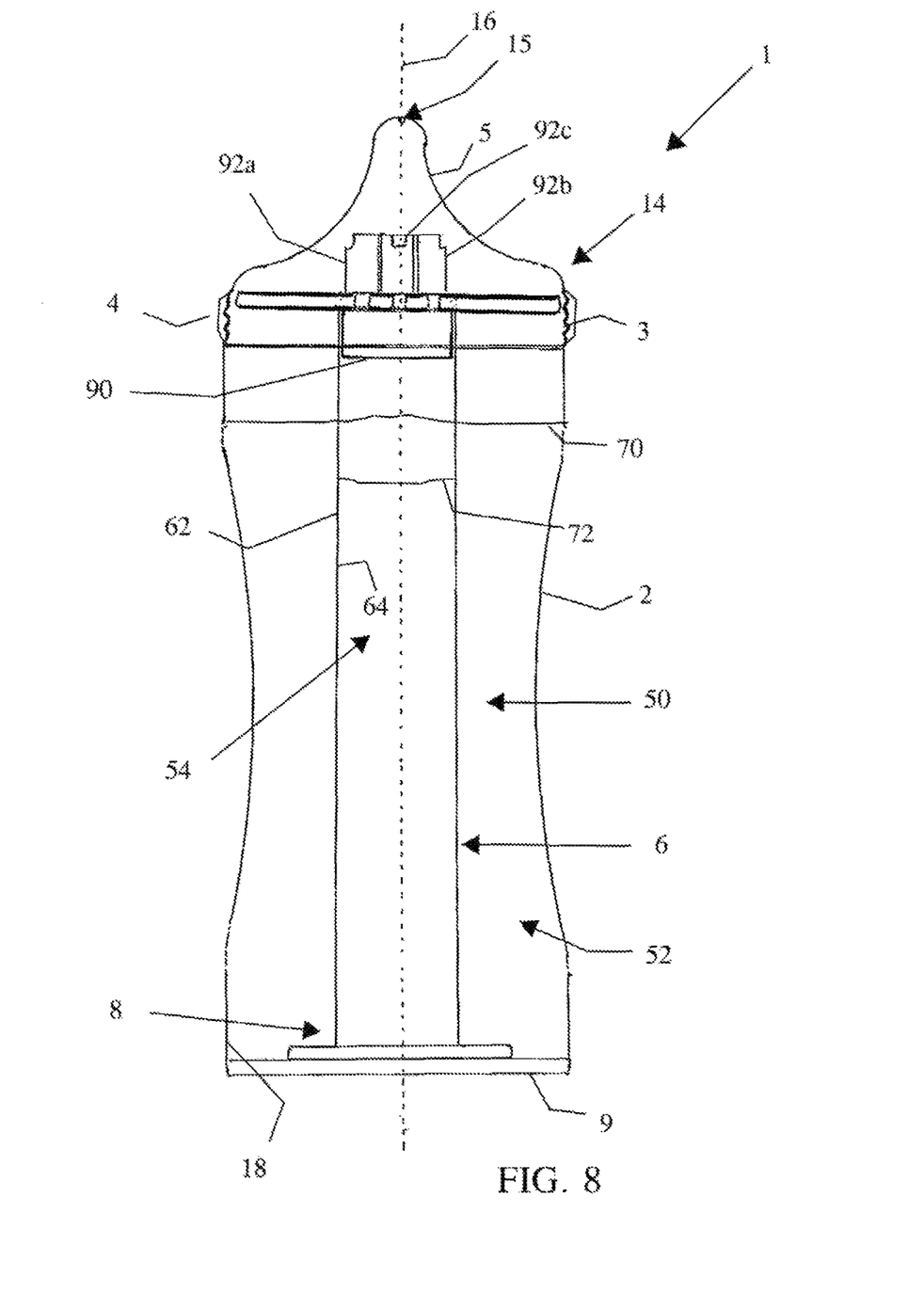
FIG. 8 is an elevation view of an embodiment of the present invention.
Figure 9A:
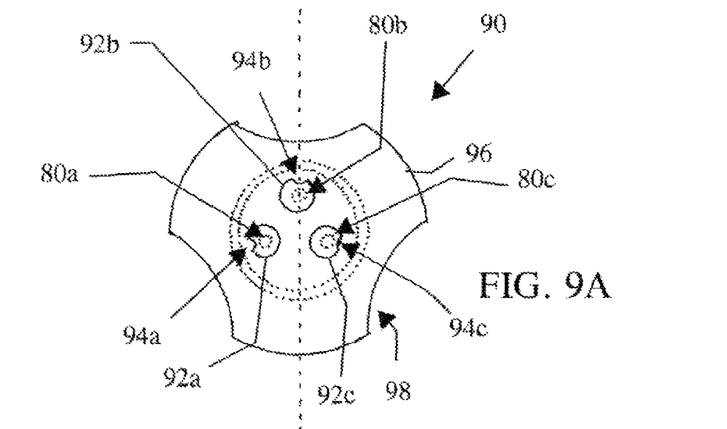
FIG. 9A is a top view of the removable cover shown in FIG. 8.
Figure 9B:
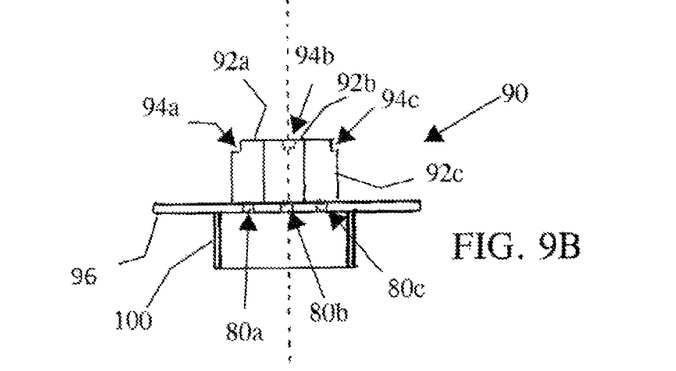
FIG. 9B is a side view of the removable cover shown in FIG. 9A.
Figure 9C:
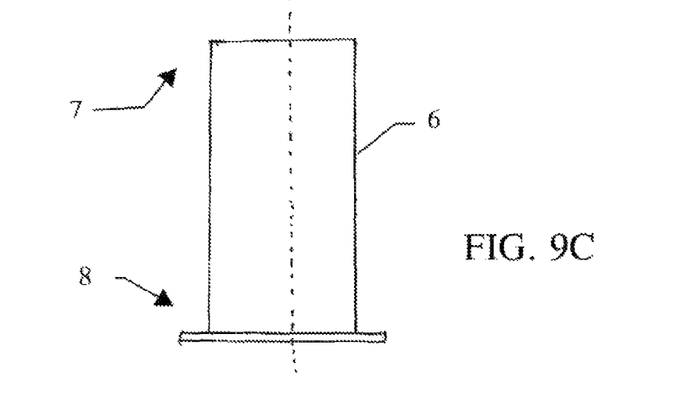
FIG. 9C is an elevation view of the rinsing device shown in FIG. 8.
Figure 10A:
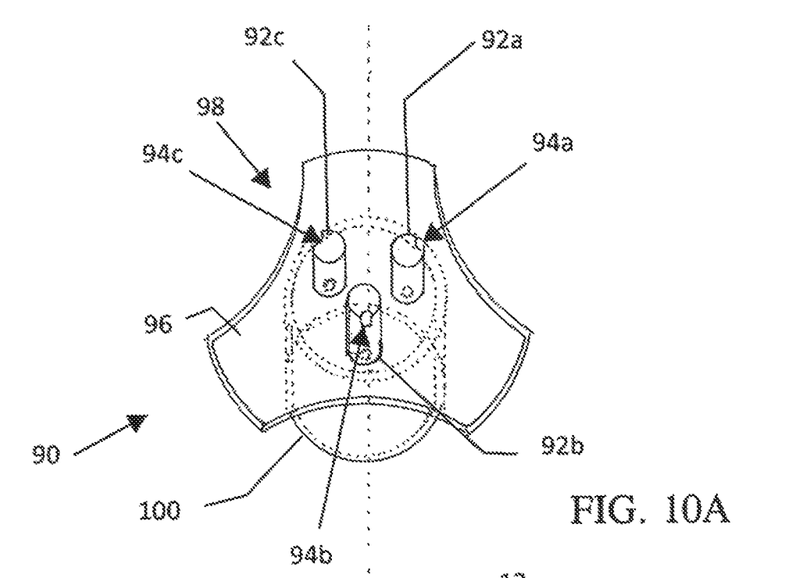
FIG. 10A is a perspective view of the cover shown in FIG. 8.
Figure 10B:
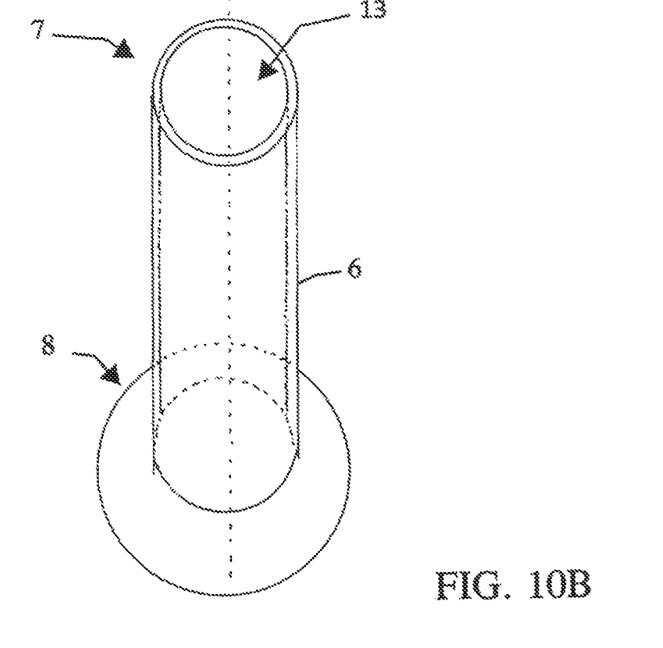
FIG. 10B is a perspective view of the rinsing device shown in FIG. 8.

In some embodiments, the tubes 92*a-c* may be arranged vertically on the cover 90 so as to form a perpendicular angle with the top surface of the cover 90 as shown in FIGS. 8, 9A, and 9B. In some embodiments, as shown in FIGS. 5A and 5B, the tubes 92*a-c* may project at an oblique angle from the top surface of the cover 90. Being on the top surface of the cover 90, the tubes 92*a-c* are able to project deeper into the nipple 5. This allows more of the first liquid 70 to be dispensed before the second liquid 72 is dispensed from the rinsing device 50. Since the tubes 92*a-c* are able to project into the nipple 5, the amount of the first liquid 70 that remains before the second liquid 72 is dispensed could be less than the volume of the nipple. In some embodiments, the amount of the first liquid 70 that remains before the second liquid b is dispensed can even be reduced to the volume of the bulbous tip of the nipple.

Figure 6:
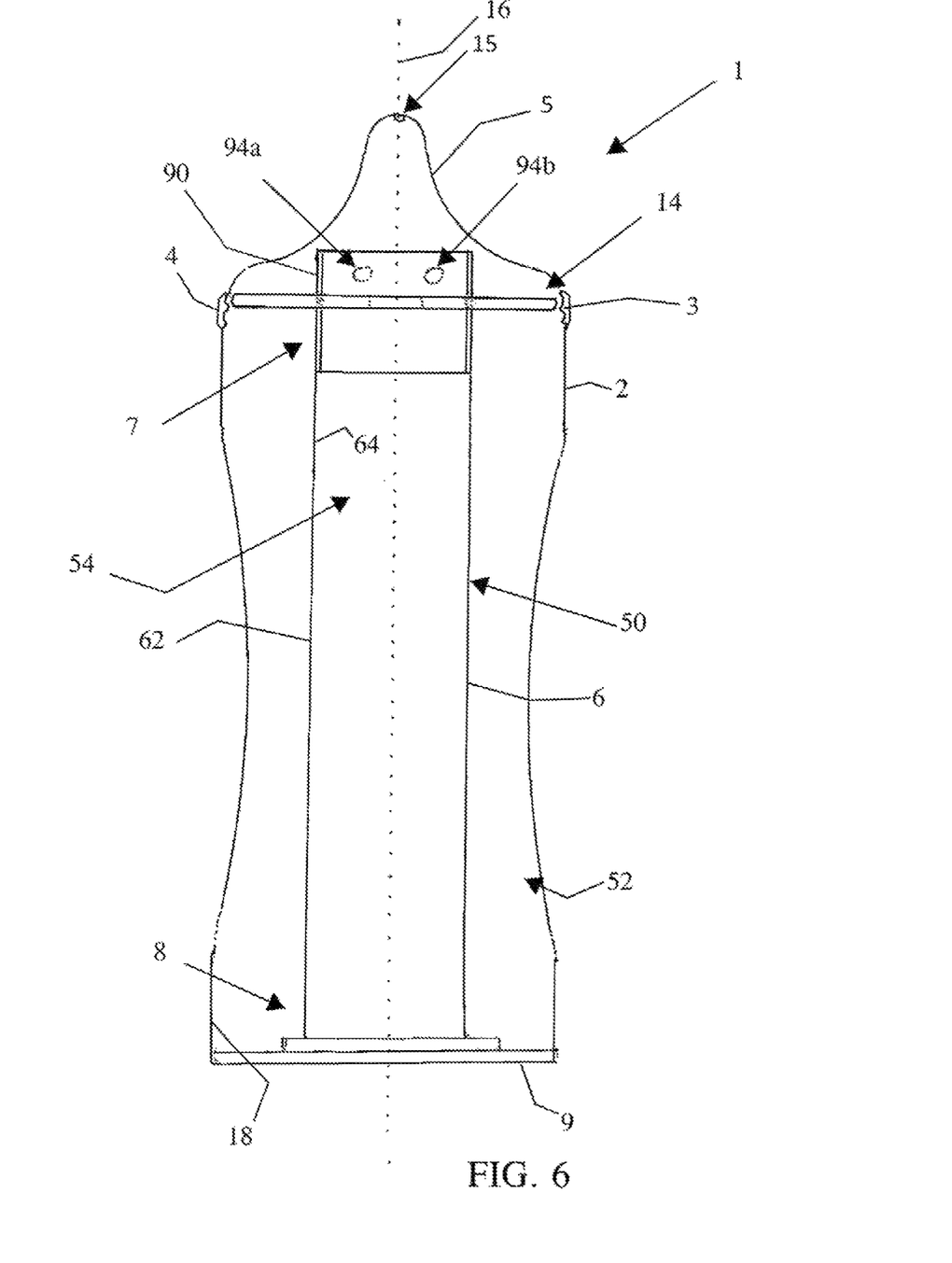
FIG. 6 is an elevation view of an embodiment of the present invention.
Figures 7A, 7B:
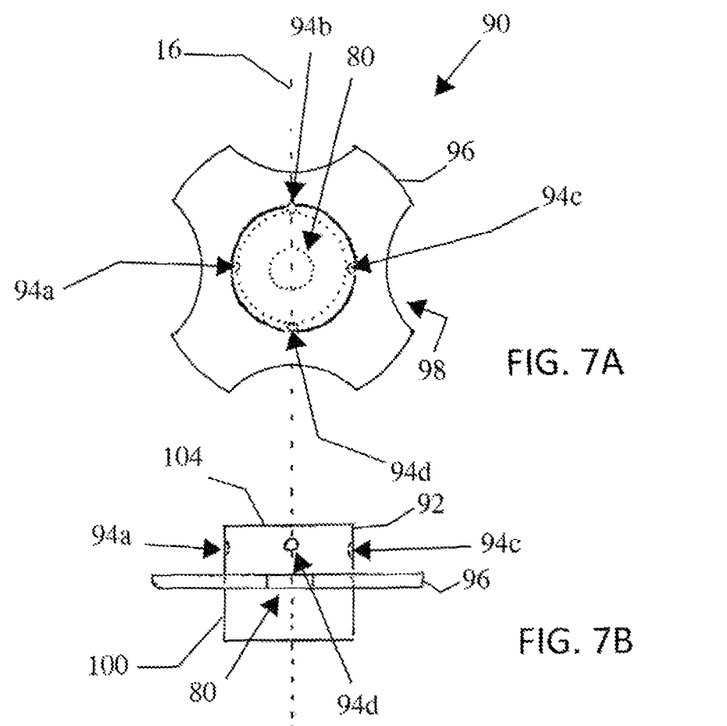
FIG. 7A is a top view of the removable cover shown in FIG. 6.
FIG. 7B is a side view of the removable cover shown in FIG. 7A.
Figure 7C:
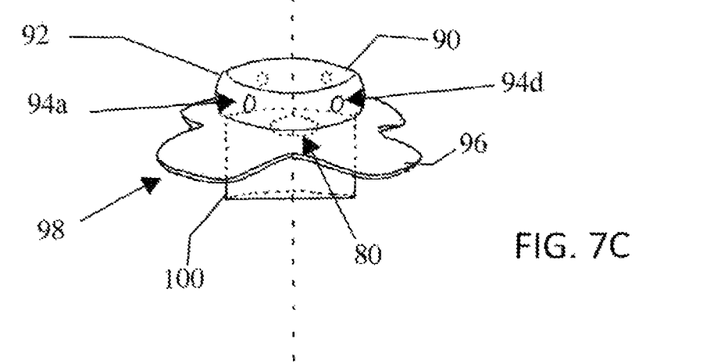
FIG. 7C is a perspective view of the removable cover shown in FIG. 7A.

In another embodiment, as shown in FIGS. 6-7*c*, the removable cover 90 may have a single, large tube 92 protruding above the extension 96. The tube 92 may be an extension of the side wall 100 of the cover 90. The tube 92 may have one large opening 94*a* as shown in FIG. 2. In some embodiments, the top of the tube 92 may be closed, and the tube 92 may comprise a plurality of smaller openings 94*a-d*. The openings 94*a-d* may be positioned on the side wall 100 of the tube 92. A cap 104 may be used to seal the top of the removable cover 90. The openings 94*a-d* may be evenly and angularly spaced apart from each other around the cylindrical sidewall 100. So, in this example having four openings 94*a-d*, each opening 94*a-d* may be angularly spaced apart by approximately 90 degrees apart from each other. A dispensing hole 80 allows the fluid to travel from the dispensing tube 50 through the cover 90. The remaining essential features are the same as or similar to that of the previous embodiments.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A nursing bottle for automatically rinsing a baby's teeth, comprising:
   a. a bottle for storing a first liquid, the bottle having an open end for receiving the first liquid and an end wall opposite the open end;
   b. a nipple mounted on the open end of the bottle, the nipple comprising a discharge hole; and
   c. a rinsing device comprising at least one side wall for storing a second liquid, the rinsing device having a dispensing end, and a closed end opposite the dispensing end, wherein the rinsing device is configured to fit completely inside the bottle with the dispensing end of the rinsing device adjacent to the open end of the bottle, the rinsing device defining a plurality of uncovered openings adjacent the dispensing end, wherein the rinsing device and the bottle are configured such that when the bottle is inverted, the plurality of uncovered openings remain submerged in the first liquid until a substantial amount of the first liquid has been dispensed so that the second liquid remains in the rinsing device until at least one of the uncovered openings is exposed to air, wherein rinsing device comprises a plurality of tubes, one tube positioned on at least one side wall at one dispensing hole, each tube being hollow and having at least one opening of the plurality of uncovered openings thereby creating fluid communication with its respective dispensing hole.

2. The nursing bottle of claim 1, wherein the dispensing holes and their respective tubes are evenly and angularly spaced apart about the at least one side wall.

3. The nursing bottle of claim 2, wherein the rinsing device comprises a main opening at the dispensing end, and a cover configured to attach to the dispensing end to cover the main opening.

4. The nursing bottle of claim 3, wherein the rinsing device further comprises an extension extending radially outwardly towards a side wall of the bottle to minimize lateral movement of the rinsing device while inside the bottle.

5. The nursing bottle of claim 4, wherein the extension defines a gap between the cover and the side wall of the bottle.

6. A nursing bottle for automatically rinsing a baby's teeth, comprising:
   a. a bottle for storing a first liquid, the bottle having an open end for receiving the first liquid and an end wall opposite the open end;
   b. a nipple mounted on the open end of the bottle, the nipple comprising a discharge hole;
   c. a rinsing device comprising at least one side wall for storing a second liquid, the rinsing device having a dispensing end, and a closed end opposite the dispensing end, wherein the rinsing device is configured to fit inside the bottle with the dispensing end of the rinsing device adjacent to the open end of the bottle, the rinsing device comprising a plurality of uncovered openings adjacent to the dispensing end, wherein the rinsing device and the bottle are configured such that when the bottle is full of the first liquid and inverted, the plurality of uncovered openings remain submerged in the first liquid, and when an amount of the first liquid has been dispensed to expose at least one uncovered opening to air, the second liquid begins dispensing, wherein the rinsing device comprises a main opening at the dispensing end, and a cover configured to attach to the dispensing end to cover the main opening, wherein the plurality of uncovered openings are on the cover.

7. The nursing bottle of claim 6, wherein the cover comprises an extension extending radially outwardly towards a side wall of the bottle to minimize lateral movement of the rinsing device while inside the bottle.

8. The nursing bottle of claim 7, wherein the cover defines a gap between the cover and the side wall of the bottle.

9. The nursing bottle of claim 6, wherein the cover comprises a plurality of tubes, one tube positioned at a dispensing hole, each tube being hollow with at least one of the plurality of uncovered openings being on each tube and having fluid communications with its respective dispensing hole.

10. The nursing bottle of claim 9, wherein the plurality of dispensing holes and their respective tubes are evenly and angularly spaced apart about the cover.

11. The nursing bottle of claim 9, wherein the plurality of tubes are perpendicular to the cover.

12. A rinsing device configured for a nursing bottle, the rinsing device comprising:
   a. at least one side wall;
   b. a dispensing end;
   c. a closed end opposite the dispensing end, wherein the rinsing device is configured to fit inside the nursing bottle with the dispensing end of the rinsing device adjacent to an open end of the bottle, the rinsing device defining a plurality of openings adjacent the dispensing end, the plurality of openings angularly spaced apart about the rinsing device;
   d. a main opening at the dispensing end; and
   e. a cover configured to attach to the dispensing end to cover the main opening, wherein at least one of the plurality of openings is on the cover.

13. The rinsing device of claim 12, wherein the rinsing device comprises an extension extending radially outwardly towards a side wall of the nursing bottle to minimize lateral movement of the rinsing device while inside the nursing bottle.

14. The rinsing device of claim 12, wherein the cover comprises:
   a. a plurality of dispensing holes evenly and angularly spaced apart; and
   b. a plurality of tubes, one tube attached to the cover at one dispensing hole, wherein at least one opening of the plurality of openings is on each tube and in fluid communication with its respective dispensing hole.

15. The rinsing device of claim 12, wherein the at least one side wall of the rinsing device defines a plurality of dispensing holes evenly and angularly spaced apart about the at least one side wall, wherein the at least one side wall further comprises a plurality of tubes, one tube attached to the at least one side wall at one dispensing hole, wherein the at least one opening is each tube and in fluid communication with its respective dispensing hole.

* * * * *